Figure 1:
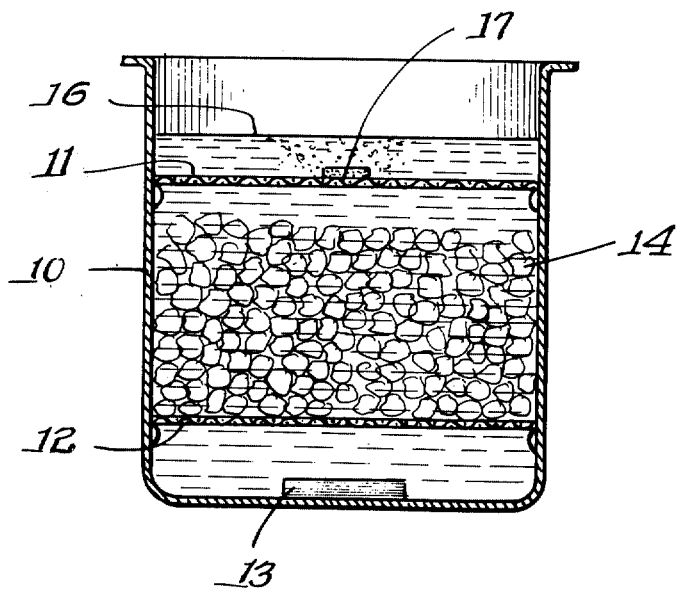

United States Patent [19]

Schmitt

[11] 4,004,036

[45] Jan. 18, 1977

[54] EFFERVESCENT MOLDED TRITURATE TABLETS

[75] Inventor: William H. Schmitt, Elmhurst, Ill.

[73] Assignee: Alberto Culver Company, Melrose Park, Ill.

[22] Filed: Mar. 20, 1970

[21] Appl. No.: 21,512

Related U.S. Application Data

[63] Continuation of Ser. No. 553,989, May 31, 1966, abandoned.

[52] U.S. Cl. .............................. 426/285; 264/122; 424/230; 426/548; 426/561; 426/562; 426/591; 426/658

[51] Int. Cl.² .................... A23L 1/22; A23L 1/236; A23L 2/40

[58] Field of Search ............. 99/78, 79, 66, 141 R, 99/141 A; 424/44; 252/1, 4, 188.3; 264/122, 232, 340, 344; 426/285

[56] References Cited

UNITED STATES PATENTS

| | | | |
|---|---|---|---|
| 1,450,865 | 4/1923 | Pele | 424/44 |
| 1,526,981 | 2/1925 | Heyl | 424/44 |
| 2,999,293 | 9/1961 | Taff et al. | 252/188.3 |
| 3,105,792 | 10/1963 | White | 424/44 |

OTHER PUBLICATIONS

Remington, Practice of Pharmacy, 12 Ed., 1961, pp. 441, 442, 460.
Remington, Practice of Pharmacy, 12 Ed., 1961, pp. 458–459.

*Primary Examiner*—Morris O. Wolk
*Assistant Examiner*—Sidney Marantz
*Attorney, Agent, or Firm*—Wallenstein, Spangenberg, Hattis & Strampel

[57] ABSTRACT

Preparation of effervescent molded triturate tablets which are rapidly disintegratable and soluble or dispersible in hot or cold aqueous media, said tablets comprising a mixture including two separate, originally pulverulent materials, which are capable of reacting in the presence of water to produce a gas, for instance, sodium bicarbonate and citric acid, the tablets being characterized by the presence of a substantial percentage of voids, generally in the range of 15% to 35%, in the interior of said tablet resulting from the limited interaction of a very minor proportion of said separate, originally pulverulent materials during the production of said molded tablet.

8 Claims, 5 Drawing Figures 43.75 x Cross section of a typical Effervescent Tablet according to present invention.

100 x Cross section of a typical Effervescent Tablet according to present invention.

43.75 x Cross section of a commercial Compressed Sweetener Tablet 43.75 x Cross section of a commercial non-effervescent Molded Saccharin Tablet

EFFERVESCENT MOLDED TRITURATE TABLETS

This application is a continuation of application Ser. No. 553,989, filed May 31, 1966, now abandoned.

This invention relates to the production of effervescent molded triturate tablets which are characterized not only by being rapidly disintegratable and soluble in hot aqueous media but, in addition, disintegrate and dissolve rapidly in cold or iced water or cold or iced beverages such as iced coffee and iced tea.

It has heretofore been well known, and is currently being practiced widely commercially, to produce sweetener tablets by admixing gas-forming ingredients, such as sodium bicarbonate and citric acid, with a sweetener or mixture of sweeteners, such as saccharine or cyclohexane sulfamic acid or salts thereof, said ingredients being in powdered pulverulent form, and compress them into tablets by conventional tablet presses, such as a Stokes double rotary press. The resulting tables, when added to a beverage such as coffee or tea, disintegrate and the disintegration is hastened by reason of the fact that the sodium bicarbonate and the citric acid react in the presence of the water in the coffee or tea to produce gaseous carbon dioxide which produces effervescence and which speeds up the disintegration of the tablet and the final solution of the sweetener or sweeteners. In the usual commercial production of such compressed sweetener tablets, all of the ingredients comprising the tablet mix, including a binder, are granulated except the sodium bicarbonate and the lubricant. The granulated mass is dried, screened, and ground to desired particle size, then the sodium bicarbonate and the lubricant are added with admixing and the resulting mass is then compressed into tablets.

Compressed tablets made as described above, although in wide commercial use as stated, are characterized by a number of objectionable features. Commonly the tablet lubricant and/or the tablet binder are incompatible with the constituents of various drinks or beverages to which the tablets are added as, for instance, tea and especially iced tea. The result is that undesirable layers or films or insoluble deposits form which are unsightly. Furthermore, effervescence is slow and tablet dissolution times are unduly long, especially where the drink or beverage is cold as with iced tea. In the case of compressed effervescent detergent tablets, the same dissolve quite slowly, are friable if compressed with too little pressure, and tend to leave a scum in the water if an insoluble lubricant is used in the making of said tablets. In the case of compressed effervescent analgesic alkalizing tablets, the dissolution rate is quite slow in cold water and, further, the tablets tend to break rather easily.

It is recognized that it has been known to produce effervescent tablets which are asserted to disintegrate or dissolve rapidly in water, as shown, for instance, in U.S. Pat. Nos. 1,450,865; 2,105,690; 2,540,253; 2,985,562; 2,999,293; 3,102,075; 3,105,792 and 3,136,692. None of the tablets of these patents corresponds, overall, to the effervescent molded triturate tablets of the present invention, as is particularly apparent in relation to their solubility or disintegratability characteristics in cold water such as iced water or iced beverages such as coffee or tea coupled with their freedom from causing haze or scums in such beverages. Thus, for instance, in the case of U.S. Pat. No. 1,450,865, the porous granules thereof, although themselves rapidly dissolved in water, are not tablets; and when said porous granules are compressed into tablets as stated in said patent, and using conventional compressed tableting pressures (punch face pressure) such as 5000 lbs/in.$^2$, such tablets exhibit substantially no voids as against approximately 29% voids utilizing a similar formulation to that of said patent but producing effervescent molded triturate tablets in accordance with the present invention. Furthermore, such compressed tablets, made according to said patent, require substantially extended periods of time to dissolve in iced water in comparison with effervescent molded triturate tablets of the same size made in accordance with the present invention.

Analogous situations obtain with respect to the other patents referred to above, which are, fundamentally, directed to the production of effervescent compressed tablets or to granules which are then compressed into tablets. In none of said tablets are there the substantial number of voids which are present in the effervescent molded triturate tablets of the present invention coupled or in combination with the rapid solubility or disintegratability properties in iced water or iced beverages and non-hazing and non-scumming properties which characterize the effervescent molded triturate tablets of the present invention.

It has been found, in accordance with the present invention, that very substantially improved tablets, in the form of effervescent molded triturate tablets, of a structure described in detail below, can be obtained by a procedure comprising, generally speaking, providing a mixture of powdered or pulverulent materials containing two separate ingredients capable of reacting in the presence of water to produce a gas, triturating said mixture to form a moldable mass with a volatile organic solvent ingredient in which at least one of said pulverulent materials is at least partially soluble, molding said mass into tablet form, said separate gas-forming ingredients interacting to a substantially limited extent to form a small amount of gas in each tablet, and then removing said organic solvent from said tablets, the gas serving to form a substantial number of voids in the interiors or bodies of said tablets. In its more limted and particularly preferred aspects, the procedure involves triturating a mixture of pulverulent materials which includes a carbonate or bicarbonate, especially sodium bicarbonate, and a carboxylic acid, especially citric acid, with a volatile organic solvent ingredient to form a moldable mass, at least one of the pulverulent materials being at least partially soluble in said organic solvent ingredient, molding said mass into tablet form, said carbonate or bicarbonate and carboxylic acid interacting to a substantially limited extent to form a small amount of carbon dioxide gas in each tablet, and then removing said organic solvent from said tablets, the carbon dioxide gas serving to form a substantial number of voids in the interiors or bodies of said tablets.

The final effervescent molded triturate tablets, as is more fully pointed out below, are characterized by being rapidly disintegratable and soluble or dispersible not only in hot aqueous media but, also, to a highly unusual extent, in cold or iced aqueous media. Indeed, for instance, at 0°–2° C, the rate of dissolution of the effervescent molded triturate tablets of the present invention is generally from at least 5 to as much as 100 times greater than various effervescent compressed tablets now being commercially marketed. The rate of dissolution of the effervescent molded triturate tablets of the present invention is markedly greater at all temperatures than heretofore known effervescent compressed tablets. Since no tablet lubricant is required in the production of said effervescent molded triturate tablets and, therefore, is most desirably not utilized, the incompatibility characteristics of prior effervescent compressed tablets are obviated. The unusually high rate of dissolution of the effervescent molded triturate tablets of the present invention, compared to that of the known effervescent compressed tablets of the type referred to above, is due, among other things, to the substantial percentage of voids in the interior of the tablets of the present invention contributed in appreciable part by the gas which is formed through interaction between the gas-forming ingredients, for instance, the sodium bicarbonate and the citric acid, which takes place during and under the conditions of the production of said effervescent molded triturate tablets, all as will be more fully described below.

It is important to the achievement of the results obtained by the present invention that, in the production of the effervescent molded triturate tablets, a small, limited interaction takes place between the gas-forming ingredients during the production of said effervescent molded triturate tablets so as to provide the additional voids in the interior of said tablets over and above those which are otherwise formed by reason of the volatilization of the organic solvent. To this end, therefore, a limited amount of water or moisture must be present to enable the interaction to take place between the gas-forming ingredients. Such water or moisture is most advantageously provided by utilizing volatile organic solvents which contain small amounts of water or by incorporating small proportions of water into an otherwise essentially anhydrous volatile organic solvent. While the water content may be as high as about 10%, by weight, based on the volatile organic solvent used in the production of the molded tablets, it is not desirable to employ such high percentages because they tend to cause stickiness in the tablet mass with resulting mechanical difficulties in the tablet molding operation. Furthermore, the higher percentages of water result in the production of low density molded tablets whose porosity is unusually high. It is advantageous, therefore, generally speaking, not to exceed about 3% of water. While the lower ranges of water content in the voltatile organic solvent are also quite variable, and may, for instance, be as low as about 0.05% or even somewhat lower, it is, generally speaking, desirable that the water content be at least about 0.25%. A water content in the range of 0.056% to 10% in the volatile organic solvent, coupled with the use of 15 volume % based upon the weight of the tablet ingredients, corresponds to the presence of from 0.0084% to 1.5% water, by weight, in the wet moldable tablet mass.

In certain instances, anhydrous volatile organic solvents can be utilized, or those which while characterized as anhydrous actually contain small percentages of water, and the moisture in the air, particularly under conditions of reasonable or fairly high relative humidity, can at least to some extent be relied upon to impart moisture sufficient to bring about limited reaction between the gas-forming ingredients to form the added voids in the interiors of the final effervescent molded triturate tablets. Generally, however, for optimum results and for effective controls, it will be found to be most advantageous to use controlled amounts of water through incorporation into the volatile organic solvent.

As illustrative of the effects of water contents in the volatile organic solvent in dissolution times of effervescent molded triturate tablets made pursuant to the present invention, a series of such tables was made from 2.355 parts sodium saccharine powder, 35.345 parts sodium cyclamate powder, 35.3 parts sodium bicarbonate USP powder and 27 parts citric acid anhydrous powder, said parts being by weight, in which the mixed powders were triturated with 0.15 volumes of triturating solution. The date, including the resulting dissolution times of the molded tablets when added to 200 cc. of water at 0°–2° C, are set out below in Table I.

TABLE I

| % $H_2O$ in 2-propanol | Tablet Density (g./in$^3$) | Dissolution Tablet (Seconds) |
| --- | --- | --- |
| 0.056 | 19.12 | 178 |
| 2.5 | 18.55 | 160 |
| 7.5 | 16.4 | 143 |
| 10 | 14.10 | 110 |

As has been pointed out above, the percentage of voids in the effervescent molded triturate tablets of the present invention is enhanced by permitting or causing a limited interaction to take place, in the presence of water or moisture, between the gas-forming ingredients whereby to form a limited amount of a gas and resulting voids in the interior of the tablets during the production thereof. While the percentage of water or moisture will influence the precise character of the effervescent molded triturate tablet, with particularly high percentages of water causing the formation, on drying, of puffy tablets with a very low density, for instance as low as 10% of that of conventional compressed tablets, it is particularly desirable to avoid such a condition and generally speaking, therefore, it is advantageous to so regulate the water content, and the overall percentage of voids, so that the effervescent molded triturate tablets have a density in the range of 60% to 90% of the density of conventional compressed tablets of otherwise corresponding composition. The percentage of voids in the effervescent molded triturate tablets of the present invention is generally in the range of 15 to 35% but, more desirably, will fall within the range of 15 to 20%. The following Table II shows the densities and % voids in a conventional effervescent compressed sweetener tablet (Tablet No. 1) in which the % voids is arbitrarily set at zero for comparison purposes, and in effervescent molded triturate sweetener tablets made in accordance with the present invention, using different percentages of water added to the volatile organic solvent.

TABLE II

| Tablet No. | % Water Added to Organic Solvent | Tablet Density (g./in$^3$) | % Voids |
| --- | --- | --- | --- |
| 1 | — | 22.05 | 0 for comparison |
| 2 | 0 | 19.12 | 12.3 |
| 3 | 2.5 | 18.55 | 15.8 |
| 4 | 5 | 16.04 | 27.3 |
| 5 | 10 | 14.10 | 36 |

The gas-forming pulverulent ingredients can be of variable character. In the usual case, they will comprise carbonates or bicarbonates, on the one hand, and carboxylic acids, on the other hand. The carbonates or bicarbonates will generally be those of the alkali metals, such as sodium, potassium and lithium but, in the usual case, for economic and other reasons, sodium bicarbonate will be the bicarbonate of choice. The carboxylic acid will generally be a water-soluble polycarboxylic acid and, where the effervescent molded triturate tablets are intended for internal use, said carboxylic acid will, of course, be one which is non-toxic when taken internally as will also be the case with the carbonate or bicarbonate. Illustrative examples of suitable carboxylic acids are citric acid, tartaric acid, succinic acid, maleic acid, fumaric acid, adipic acid, itaconic acid and tricarballylic acid. The proportions of the gas-forming ingredients employed in the effervescent molded triturate tablets are variable within very wide limits, being dependent, among other things, on the nature and intended use of the said tablets. Thus, for instance, said gas-forming ingredients may comprise substantially less than half the weight of said tablets to substantially greater than half the weight of said tablets.

Various volatile organic solvents can be used for triturating or moistening the tablet mix to produce a moldable mass, illustrative of which are ethanol, 2-propanol, chloroform, 1-butanol, and acetone, as well as mixed solvents. The solvent selected must be correlated with the tablet ingredients in the sense that at least one of the powdered or pulverulent tablet ingredients must be at least partially soluble in said organic solvent ingredient. Thus, for example, the carbonate or the bicarbonate or the citric acid, or the sweetener or analgesic or other powdered or pulverulent ingredient of the tablet mix, must be at least partly soluble in the organic solvent, or organic solvent-water solution, in order to impart form and rigidity to the molded tablet when dried. The proportion of the volatile organic solvent system utilized, in relation to the weight of the dry or pulverulent ingredients, is variable within rather wide limits, bearing in mind that, in the mixing or trituration step, it is necessary to form a moldable mass. Generally speaking, the volatile organic solvent system, depending upon the nature of the dry or pulverulent ingredients, may range from about 3 to 40 volume % of the weight of the dry or pulverulent ingredients.

To obtain a measure of the speed of dissolution for comparative purposes, a simple test apparatus was devised which is shown in FIG. 1 of the drawings. As there shown, it consists of a 4-liter beaker 10 provided with a 30-mesh screen 11 supported in the upper part of said beaker. A 20-mesh screen 12 is supported in the lower part of said beaker below which rests a 2 inches diameter Mag Bar stirrer or agitator 13. Disposed between the screens 11 and 12 are pieces of ice 14 and the beaker is filled with water to a level 16 slightly above the surface of the screen 11. The tablets, exemplified by an effervescent molded triturate tablet 17, to be tested for their speed of dissolution are dropped onto the screen 11 so as to be fully submerged in the water above said screen and then the time is measured for said tablets either to pass through said screen 11 or, if floating, are of a size estimated to be smaller than 30 mesh. The temperature of the ice-containing water is 0°–2° C which is the temperature at which substantially the slowest rate of effervescence of the effervescent tablets occurs.

The following Table III shows the speed of dissolution, using the test device of FIG. 1, of several certain commercially marketed sweetener tablets in comparison with illustrative effervescent molded triturate tablets made in accordance with the present invention. Tablets Nos. 1, 2 and 3 are effervescent compressed sweetener tablets; Tablet No. 4 is a non-effervescent molded sweetener tablet; and Tablets Nos. 5, 6 and 7 are illustrative effervescent molded triturate sweetener tablets made in accordance with the present invention.

TABLE III

| Tablet No. | Dissolution/Tablet (Seconds) | Dissolution/Gm Tablets (Seconds) |
|---|---|---|
| 1 | 7980 | 123,800 |
| 2 | 2580 | 35,600 |
| 3 | 900 | 5,240 |
| 4 | 1200 | 12,000 |
| 5 | 93 | 1,120 |
| 6 | 80 | 942 |
| 7 | 100 | 1,097 |

In the following Table IV, similar tests as to speed of dissolution were run, but at different temperatures, in 250 ml of water, of certain commercially marketed sweetener tablets in comparison will illustrative effervescent molded triturate tablets made in accordance with the present invention. Tablets Nos. 1, 2 and 3 are effervescent compressed sweetener tablets. Tablets Nos. 4, 5 and 6 are illustrative effervescent molded triturate tablets made in accordance with the present invention.

TABLE IV

| Tablet No. | Dissolution/ Tablet 12–13° C (Seconds) | Dissolution/ Tablet 24° C (Seconds) | Dissolution/ Tablet 45° C (Seconds) |
|---|---|---|---|
| 1 | 320 | 110 | 30 |
| 2 | 540 | 195 | 28 |
| 3 | 320 | 110 | 30 |
| 4 | 21 | 13 | 6 |
| 5 | 32 | 13 | 6 |
| 6 | 35 | 17 | 6 |

Effervescent molded triturate tablets of the present invention can be made in various hardnesses and densities. Generally speaking, as the water content in the volatile organic solvent increases the tablet hardness increases and the tablet density decreases. Hence, by varying the composition of the volatile organic solvent, and the amount thereof, employed in the production of the effervescent molded triturate tablets of the present invention, the exact hardness and density of said tablets can be controlled. The following Table V shows the effect of water content in the volatile organic solvent on the hardness of the tablets.

TABLE V

| Tablet No. | % Water in Organic Solvent | Hardness (SCA) (Kg.) |
|---|---|---|
| 1 | 0 | 4 |
| 2 | 1 | 4–5 |
| 3 | 2 | 5–6 |
| 4 | 5 | 8 |
| 5 | 7.5 | 10 |
| 6 | 10 | 8 |

The following examples are illustrative of effervescent molded triturate tablets made in accordance with the present invention. It will be understood that numerous other effervescent molded triturate tablets of different composition can be made utilizing variant ingredients, proportions and other conditions, all within the scope of the guiding principles and teachings disclosed herein. All parts listed are by weight except where otherwise specifically stated.

EXAMPLE 1

| Effervescent Molded Triturate Sweetener Tablet | Parts |
|---|---|
| Sodium Saccharine Powder | 2.355 |
| Sodium Cyclamate Powder | 35.345 |
| Sodium Bicarbonate USP Powder | 35.3 |
| Citric Acid Anhydrous Powder | 27 |

The dry powders are mixed to provide a substantially uniform mixture. Then there is admixed therewith 0.15 volume of a mixture of anhydrous 2-propanol (containing about 0.05% water) and water (in the ratio of 97.5 parts of the 2-propanol to 2.5 parts deionized water, by volume), to produce a damp mass. The mass is pressed into tablet mold, extruded and dried at 50° C. Smooth tablets of 90 mg. each are obtained having 6–8 Kg. hardness. Dissolution — 17 sec. at 24° C in 200 cc water.

EXAMPLE 2

| Large Effervescent Molded Triturate Sweetener Tablet | Parts |
|---|---|
| Sodium Saccharine Powder | 2.355 |
| Sodium Cyclamate Powder | 35.345 |
| Sodium Bicarbonate USP Powder | 35.3 |
| Citric Acid Anhydrous Powder | 27 |

The dry powder mixture is admixed with 0.15 volume of 2-propanol (containing about 0.5% water) to produce a damp mass which is pressed into a 1 inch tablet mold, extruded and dried at 50° C. A very hard, 5.78 g tablet is obtained that dissolves rapidly in cold water. It is equivalent in sweetness to ½ cup of sugar.

EXAMPLE 3

| Effervescent Molded Triturate Beverage Tablet | Parts |
|---|---|
| Sodium Cyclamate Powder | 10.2 |
| Sodium Saccharine Powder | 0.4 |
| Sodium Bicarbonate USP Powder | 26.5 |
| Citric Acid Anhydrous Powder | 61.2 |
| Dragoco S.D. Lime N-672 | 1.7 |

The dry powder mixture is admixed with 0.15 volume of 2-propanol (containing about 0.4% water) to produce a damp mass which is pressed into a 1 inch tablet mold, extruded and dried at 50° C. Very hard tablets are obtained each weighing 5.375 g. One tablet placed in 1 pint of cold water effervesces rapidly, forming a pleasant carbonated drink with a pH of 3.5–4.

EXAMPLE 4

| Effervescent Molded Triturate Sugar Tablet | Parts |
|---|---|
| Sucrose XF - comminuted through 80 mesh | 73 |
| Sodium Bicarbonate USP Powder | 15.7 |

-continued

| Effervescent Molded Triturate Sugar Tablet | Parts |
|---|---|
| Citric Acid Anhydrous | 11.3 |

The dry powder mixture is admixed with 0.203 volume of anhydrous 2-propanol (containing about 0.05% water) to produce a damp mass which is pressed into a 1 inch tablet mold, extruded and dried at 50° C. The tablets are very hard, each weighs 5.2 g. (3.8 g. Sucrose) and dissolves completely at 0°–2° C in 300 sec. It places 15% more sugar in solution in less than half the time that it takes with a commercial sugar cube weighing 3.32 g. having dimensions of 0.15 × 0.527 × 0.515 inch. The latter cube dissolves in 0°–2° C water in 630 sec.

EXAMPLE 5

| Effervescent Molded Triturate Detergent Tablet | Parts |
|---|---|
| Commercial Synthetic Detergent Granules | 50 |
| Sodium Bicarbonate USP Powder | 29 |
| Citric Acid Anhydrous Powder | 21 |

The dry powder mixture is admixed with 0.125 volume of 2-propanol (containing about 0.6% water) to produce a damp mass which is pressed into a 1 inch tablet mold, extruded and dried at 50° C. A hard tablet, 5.35 g., is obtained which effervesces steadily in 45° C tap water to a clear solution in 240 sec.

EXAMPLE 6

| Effervescent Molded Triturate Analgesic Alkalizing Tablet | Parts |
|---|---|
| Aspirin | 5.6 |
| Sodium Bicarbonate USP | 53.4 |
| Citric Acid Anhydrous | 31.0 |
| Mono-Calcium Phosphate | 10.0 |

The dry powder mixture is admixed with 0.14 volume of 2-propanol (containing about 0.25% water) to produce a damp mass which is pressed into a 1 inch tablet, extruded and dried. A hard tablet, 0.228 inch thick, 3.48 g. is obtained which dissolves in 45–53 sec. at 0°–2° C compared with 225 to 235 seconds for a commercial effervescent analgesic alkalizing tablet weighing 3.61 g.

EXAMPLE 7

| Effervescent Molded Triturate Disinfectant Tablet | Parts |
|---|---|
| Citric Acid Anhydrous | 34.7 |
| Sodium Bicarbonate USP Powder | 47.9 |
| Cetyl pyridinium Chloride | 17.4 |

The dry powder mixture is admixed with 0.037 volume of 2-propanol (containing about 0.5% water) to produce a damp mass which is pressed into a 1 inch tablet, extruded and dried at 50° C. A tablet 0.395 inch thick, 4.82 g. is obtained. When thrown into 1 gallon of water, it effervesces to make a 1:4500 solution suitable as a general disinfectant.

EXAMPLE 8

| Effervescent Molded Triturate Sweetener Tablet | |
|---|---|
| | Parts |
| Sodium Saccharine Powder | 2.355 |
| Aspartyl-phenylalanine methyl ester | 35.345 |
| Citric Acid Anhydrous Powder | 27 |
| Sodium Bicarbonate USP Powder | 35.3 |

The same procedure is followed as that of Example 1 with the production of tablets of similar properties.

Figure 2:
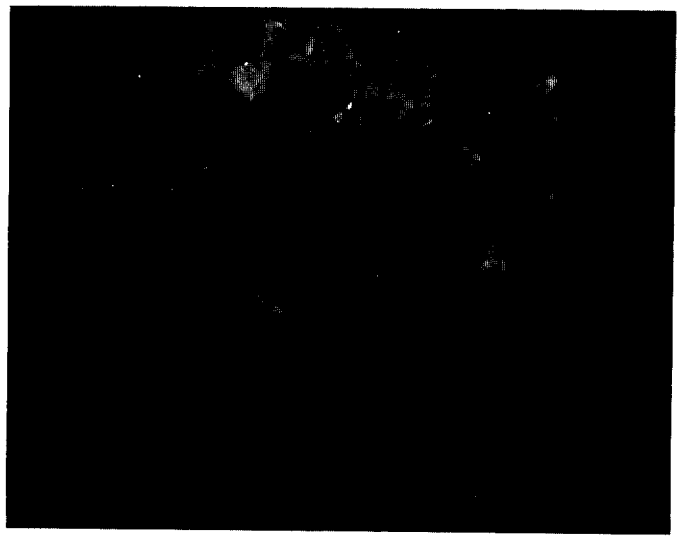
Figure 3:
Figure 4:
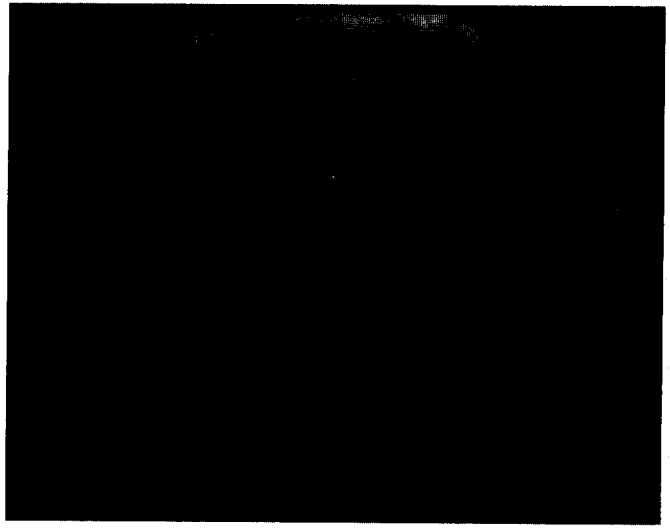
Figure 5:

In FIGS. 2 and 3, photomicrographs are shown of a cross section taken through an effervescent molded triturate sweetener tablet made in accordance with the present invention (magnifications of 43.75 $\times$ and 100 $\times$);

FIG. 4 is a photomicrograph of a cross section (43.75 $\times$) of a conventional commercial effervescent compressed sweetener tablet; and FIG. 5 is a photomicrograph of a cross section of a non-effervescent molded sweetener tablet. The materially greater content of voids in the tablets of FIGS. 2 and 3, in relation to the tablets of FIGS. 4 and 5, is apparent.

As will be seen from the foregoing examples, effervescent molded triturate tablets can be made, pursuant to the present invention, which contain, in addition to the gas-forming ingredients, various ingredients for particular uses as, for instance, artificial sweeteners or sugar substitutes such as those mentioned above as well as aspartyl dipeptide lower alkyl esters such as are shown in U.S. Pat. No. 3,475,403; beverage ingredients, flavors, sugars, detergents, drugs, germicidal and antiseptic agents such as quaternary ammonium compounds, disinfectants and, indeed, essentially any dry product which it is desired to be made into an aqueous solution or dispersion. Since the effervescent molded triturate tablets are molded, there are no practical limitations as to their size or shape and dies can readily be made to produce tablet sizes ranging from weights of a few mg. to several kilograms. The invention is particularly important for the production of effervescent molded triturate sweetener tablets for general usage in hot and cold beverages, with especial and outstanding utility for use in cold, notably iced, beverages such as coffee and tea.

In the light of the foregoing, it will be understood that the effervescent molded triturate tablets of the present invention are to be sharply distinguished from effervescent compressed tablets and, indeed, molded tablet triturates as well recognized in the art and distinguished from compressed tablets. The former, originally made from moist materials on a triturate mold and now usually made on a tablet machine, generally dissolve quite rapidly in water or aqueous liquids at room temperature or elevated temperatures, but distinctly more slowly in cold or iced water or iced beverages. Where heretofore known molded tablet triturates are prepared on so-called compression tablet machines, low or moderate pressures can be utilized, generally of the order of about 500 to about 1500 lbs, applied press pressure setting (e.g. to produce 1-inch diameter tablets), and it is generally necessary to employ mold lubricants. Compressed tablets, on the other hand, are formed by compression under substantial pressure, usually in the range of about 2,000 to about 12,000 lbs, applied press pressure setting, of powdered, crystalline or granular materials, alone or in combination with binders or adhesives, so-called disintegrators such as starch, lubricants and fillers. Such compressed tablets are generally harder than molded triturate tablets and they dissolve or disintegrate more slowly than molded or triturate tablets, and this is especially pronounced in cold or iced water or iced beverages. The United States Pharmacopeia, Seventeenth Revision, Sept. 1, 1965, pp. 794–5; The National Formulary, Twelfth Edition, Sept. 1, 1965, p. 484; Remington's Pharmaceutical Sciences, Thirteenth Edition, Mack Publishing Company, 1965, pp. 562 et seq; and Husa's Pharmaceutical Dispensing, Fifth Edition, Mack Publishing Company, 1959, pp. 55–70 are illustrative of publications relating to molded triturate tablets and compressed tablets and the manufacture thereof.

It is apparent, in the view of what has been set forth above, that no novelty is claimed per se in the broad practice of producing molded triturate tablets since, as a dosage form, they have long been known to the art, being most commonly employed in the production of hypodermic tablets and certain other drug tablets, as shown in the foregoing publications and in such publications as Wood, Tablet Manufacture (1906); Caspari, A Treatise on Pharmacy (1916); and Scoville, Art of Compounding (1914). Molded tablet triturates, of the type heretofore known, generally have been characterized by the disadvantage of high friability or softness of the tablet. If such tablets are made hard, they have a very slow rate of dissolution in water. The effervescent molded triturate tablets of the present invention are sharply differentiable in characteristics and behavior from classical molded triturate tablets which traditionally can be crushed with simple thumb and forefinger pressure. So far as has been ascertained, despite the fact that molded triturate tablets have been known for a great number of years, and despite the fact that sweetener tablets have also been known for many, many years, no one has disclosed or taught the production of effervescent molded triturate tablets which possess the structure and properties of those produced in accordance with the present invention and which dissolve rapidly in cold or iced aqueous media.

What is claimed is:

1. A method of preparing effervescent molded triturate tablets which are rapidly disintegratable and soluble or dispersible in hot or cold aqueous media, which comprises providing a mixture of pulverulent materials containing two separate ingredients capable of reacting in the presence of water to produce a gas, triturating said mixture, in the presence of a limited amount of water, to form a moldable mass with a volatile organic solvent ingredient in which at least one of said pulverulent materials is at least partially soluble, said limited amount of water not exceeding 10% by weight of said volatile organic solvent, molding said mass into tablet form, said separate gas-forming ingredients interacting to a substantially limited extent to form a small amount of gas in each tablet, and then removing said organic solvent from said tablets, said gas serving to form a substantial number of voids in the bodies of said tablets.

2. A method of preparing effervescent molded triturate tablets which are rapidly disintegratable and soluble or dispersible in hot or cold aqueous media, which comprises triturating, in the presence of a limited amount of water, a mixture of pulverulent materials which includes a carbonate or bicarbonate and a carboxylic acid with a volatile organic solvent ingredient to form a moldable mass, at least one of the pulverulent materials being at least partially soluble in said organic solvent ingredient, said limited amount of water not exceeding 3% by weight of said volatile organic solvent, molding said mass into tablet form, said carbonate or bicarbonate and carboxylic acid interacting to a substantially limited extent to form a small amount of carbon dioxide gas in each tablet, and then removing said organic solvent from said tablets, said carbon dioxide gas serving to form a substantial number of voids in the bodies of said tablets.

3. A method according to claim 2, wherein the carbonate or bicarbonate is sodium bicarbonate and the carboxylic acid is citric acid.

4. A method according to claim 3, wherein there is included in said mixture of pulverulent materials a water-soluble synthetic non-toxic sweetening agent.

5. A method according to claim 4, wherein said sweetening agent is at least one member of the group of saccharine and non-toxic water-soluble salts thereof, and aspartyl dipeptide lower alkyl esters.

6. A method according to claim 2, wherein the organic solvent comprises at least one of the group of ethanol, 2-propanol, and acetone.

7. A method according to claim 2, wherein the percentage of voids in the tablets is in the range of 15% to 35%.

8. An effervescent molded triturate tablet which is rapidly disintegratable and soluble or dispersible in hot or cold aqueous media produced in accordance with the method of claim 1.

* * * * *